(12) United States Patent
King et al.

(10) Patent No.: US 7,273,714 B2
(45) Date of Patent: Sep. 25, 2007

(54) ALKYLGUANYLTRANSFERASE ASSAYS

(75) Inventors: Ivan C. King, North Haven, CT (US); Xu Lin, Branford, CT (US)

(73) Assignee: VION Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 11/373,623

(22) Filed: Mar. 9, 2006

(65) Prior Publication Data

US 2006/0205027 A1    Sep. 14, 2006

Related U.S. Application Data

(60) Provisional application No. 60/663,454, filed on Mar. 18, 2005, provisional application No. 60/660,738, filed on Mar. 11, 2005.

(51) Int. Cl.
*C12Q 1/48* (2006.01)
*G01N 33/53* (2006.01)

(52) U.S. Cl. ......................... 435/15; 435/7.5

(58) Field of Classification Search .................. None
See application file for complete search history.

(56) References Cited

U.S. PATENT DOCUMENTS

2002/0076785 A1* 6/2002 Glotzer et al. ............. 435/196
2004/0115130 A1* 6/2004 Johnsson et al. .......... 424/1.69

OTHER PUBLICATIONS

Goodtzova et al. Activation of Human O6-Alkylguanine-DNA Alkyltransferase by DNA; Biochemistry, vol. 33, No. 28 (1994) pp. 8385-8390.*

Noll et al. Covalent Capture of a Human O6-Alkylguanine Alkyltransferase-DNA Complex Using N1,O6-Ethanoxanthosine, a Mechanism-Based CrossLinker; Nucleic Acids Research, vol. 29, No. 19 (2001) pp. 4025-4034.*

Ishibashi, et al., "Artificial Control of Nuclear Translocation of DNA Repair Methyltransferase", J. Biol. Chem. vol. 269, pp. 7645-7650 (1994).

Ishibashi, et al., "Intercellular Localization and Function of DNA Repair Methyltransferase in Human Cells", Mutat. Res. vol. 315, pp. 199-212(1994).

Citron, et al., "06-methylguanine-DNA Methyltransferase in Normal and Malignant Tissue of the Breast", Cancer Investig. vol. 12, pp. 605-610 (1994).

Kokkinakis, et al., "Role of 06-Methylguanine-DNA Methyltransferase in the Resistance of Pancreatic Tumors to DNA Alkylating Agents", Cancer Res. vol. 57, pp. 5360-5368 (1997).

Lage, et al., "Involvement of the DNA Mismatch Repair System in Antineoplastic Drug Resistance", Cancer Res. Cln. Or. vol. 125, pp. 156-165(1999)

Chinnasamy, et al., "06-Benzylguanine Potentiates The In Vivo Toxicity and Clastogenicity of Temozolomide and BCNU in Mouse Bone Marrow", Blood. vol. 89, pp. 1566-1573 (1997).

Belanich, et al., "Retrospective Study of the Correlation Between the DNA Repair Protein Alkytransferase and Survival of Brain Tumor Patients Treated with Carmustine", Cancer Res. vol. 56, pp. 783-788 (1996).

Jaeckle, et al., "Correlation of Tumor 06 Methylguanine-DNA methyltransferase Levels With Survival of Malignant Astrocytoma Patients Treated With Bis-Chloroethylnitrosourea: A Southwest Oncology Group Study", J. Clin. Ocol. vol. 16, pp. 3310-3315 (1998).

Wu, et al., "Measurement of 06-Alkylguanine-DNA Alkyltransferase Activity in Human Cells and Tumor Tissues by Restriction Endonuclease Inhibition", Cancer Res. vol. 47, p. 6229 (1987).

Gerson, et al., "06 Alkylguanine-DNA Alkyltransferase Activity in Human Myeloid Cells", J. Clin. Invest. vol. 76, p. 2106 (1985).

Kreklau, et al., "A Novel Fluorometric Oligonucleotide Assay to Measure o(6)-Methylguanine DNA Methyltransferase, Methylpurine DNA Glycosylase, 8-oxyguanine DNA Glycosylase and Abasic Endonuclease Activities: DNA Repair Status in Human Breast Carinoma Cells Overexpressing Methylpurine DNA Glycosylase", J. Clin. Nucleic Acid Res., vol. 29, p. 2558 (2001).

Noll, et al., "Covalent Capture of a Human O(6)-Alkylguanine Alkyltransferase-DNA Complex Using N(1), O(6)-ethanoxanthosine, a Mechanism-Based Crosslinker", J. Clin. Nucleic Acid Res., vol. 29, p. 4025 (2001).

* cited by examiner

*Primary Examiner*—Patricia Leith
*Assistant Examiner*—Paul Martin
(74) *Attorney, Agent, or Firm*—Law Offices of Albert Wai-Kit Chan, PLLC

(57) ABSTRACT

This invention provides a method to determine alkylguanyltransferase activity in a sample, comprising steps of placing the sample in an appropriate condition so that the AGT is functional; contacting the sample with an AGT Detector under conditions permitting the binding of AGT and AGTD to produce a signal; and measuring the signal, thereby determining the AGT activity in said sample. This invention provides different uses of this method.

17 Claims, 5 Drawing Sheets

Figure 1

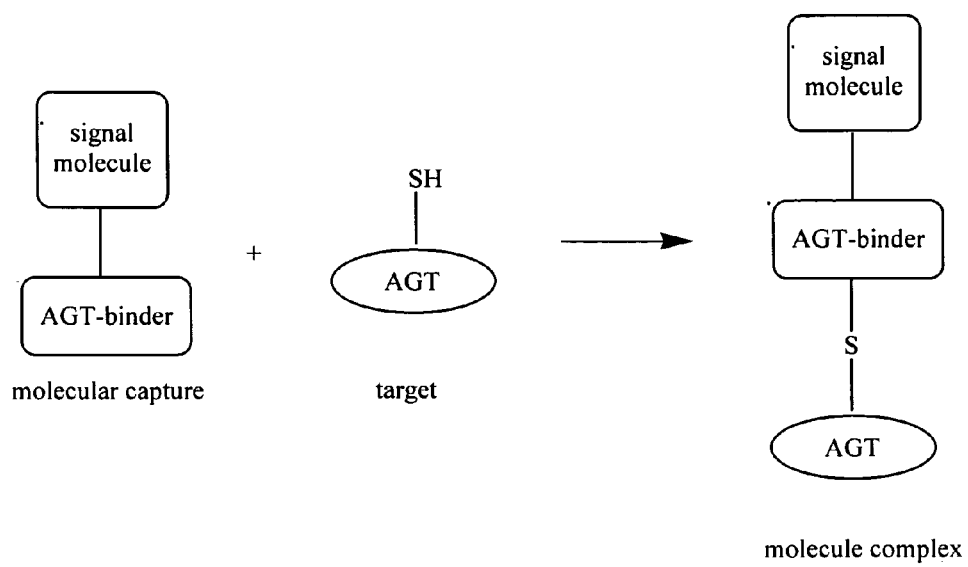

Figure 4:
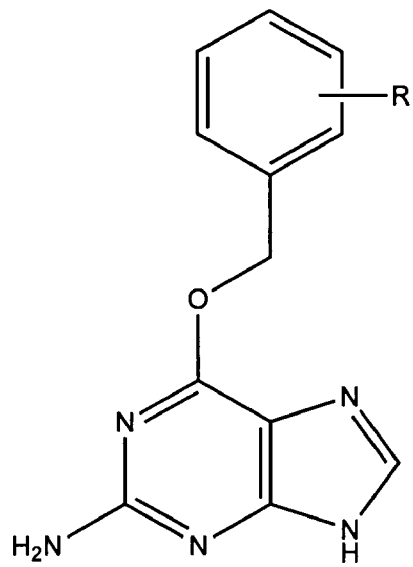

AGT-binder = O$^6$-benzylguanine (O6BG), 8-aza-O$^6$-benzylguanine,
O$^6$-(4-bromothenyl) guanine, O$^6$-alkylguanine,
N$^1$, O$^6$-ethanoxanthine (EX), and
6-alkylamino-2-aminopurine (AP), ...
native or modified oligonucleotides or conjugates or pro-drugs or co-drugs
or combination treatment with other agents such as temozolemide or BCNU
containing the above.

Signal molecule = biotin or fluorophore

Figure 2
Example of AGT-binder = EX
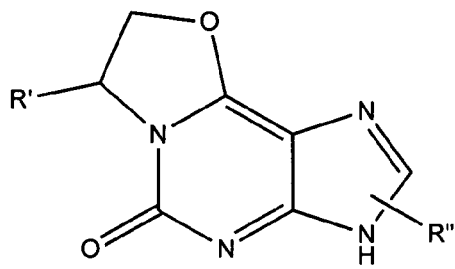
R' = H, $C_{1-4}$ alkyl
R" = (linker)-(signal molecule) at C-8 or N-9 position of the xanthine
(linker) = -[ ]-; -O-; -NH-;
-$(CH_2)_nO$- (n = 1-6); -$(CH_2)_nNH$- (n = 1-6);
-$O(CH_2)_nO$- (n = 1-6); -$O(CH_2)_nNH$- (n = 1-6);
-$NH(CH_2)_nO$- (n = 1-6); -$NH(CH_2)_nNH$- (n = 1-6);
-$(CH_2)_nCO$- (n = 1-6);
-$O(CH_2)_nCO$- (n = 1-6);
-$NH(CH_2)_nCO$- (n = 1-6); ...
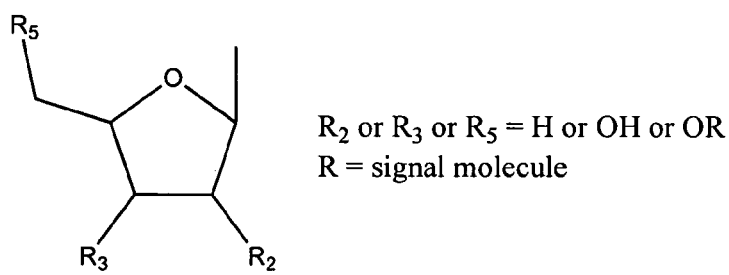
$R_2$ or $R_3$ or $R_5$ = H or OH or OR
R = signal molecule Figure 3
Example of AGT-binder = AP
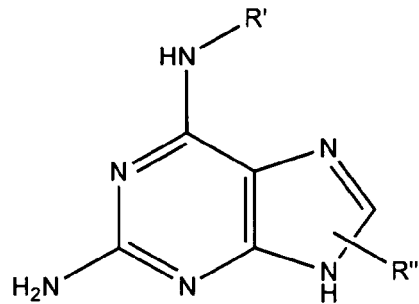
R' = $C_{1-10}$ alkyl, substituted alkyl, benzyl, substituted benzyl,
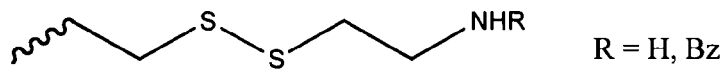
R = H, Bz
R" = (linker)-(signal molecule) at C-8 or N-9 position of the xanthine
(linker) = -[ ]-; -O-; -NH-;
-$(CH_2)_nO$- (n = 1-6); -$(CH_2)_nNH$- (n = 1-6);
-$O(CH_2)_nO$- (n = 1-6); -$O(CH_2)_nNH$- (n = 1-6);
-$NH(CH_2)_nO$- (n = 1-6); -$NH(CH_2)_nNH$- (n = 1-6);
-$(CH_2)_nCO$- (n = 1-6);
-$O(CH_2)_nCO$- (n = 1-6);
-$NH(CH_2)_nCO$- (n = 1-6); ...
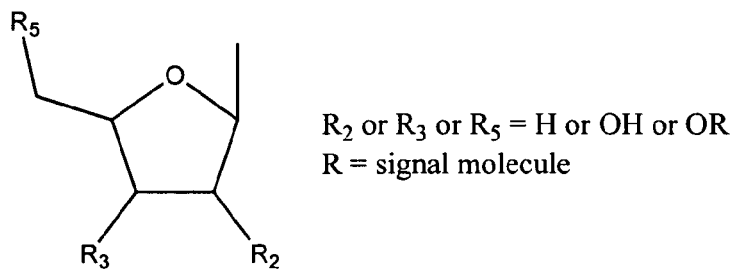
$R_2$ or $R_3$ or $R_5$ = H or OH or OR
R = signal molecule

Example of AGT-binder = O6BG

R = (linker)-(signal molecule) as a substituent of the benzyl ring (linker) = -[ ]-; -O-; -NH-;
-$(CH_2)_nO$- (n = 1-6); -$(CH_2)_nNH$- (n = 1-6);
-$O(CH_2)_nO$- (n = 1-6); -$O(CH_2)_nNH$- (n = 1-6);
-$NH(CH_2)_nO$- (n = 1-6); -$NH(CH_2)_nNH$- (n = 1-6);
-$(CH_2)_nCO$- (n = 1-6);
-$O(CH_2)_nCO$- (n = 1-6);
-$NH(CH_2)_nCO$- (n = 1-6); ...

ALKYLGUANYLTRANSFERASE ASSAYS

This application claims the benefit of U.S. Ser. No. 60/663,454, filed Mar. 18, 2005 and U.S. Ser. No. 60/660,738, filed Mar. 11, 2005. The contents the preceding applications are hereby incorporated herein by reference in their entireties.

Throughout this application, various references are referred to and disclosures of these publications in their entireties are hereby incorporated by reference into this application to more fully describe the state of the art to which this invention pertains.

BACKGROUND OF THE INVENTION

Chemotherapeutic agents that alkylate the O6 position of guanine in DNA such as Carmustine (Ishibashi, et al., J. Biol. Chem., 269: 7645-7650, 1994) 1-(2-chloroethyl)-3-cyclohexyl-1-nitrosourea, fotemustine, dacarbazine, streptozotocin, procarbazine, and temozolomide (TMZ) are used primarily to treat brain cancer, melanoma, lymphoma, and gastrointestinal cancers. The effectiveness of these agents, however, is limited by alkylguanyltransferase (AGT), a protein that repairs O6-alkylguanine adducts and is up-regulated in several tumors during progression (Ishibashi et al., Mutat. Res., 315: 199-212, 1994; Citron et al., Cancer Investig., 12: 605-610, 1994; Kokkinakis et al., Cancer Res., 57: 5360-5368, 1997).

Furthermore, selection of resistant AGT phenotypic populations after treatment with alkylating agents seems to be the reason for the recurrence of tumors of even a more resistant phenotype (Lage et al., J. Cancer Res. Clin. Oncol., 125: 156-165, 1999). Tumor resistance to DNA alkylation could be theoretically reversed with AGT inhibitors that react with and inactivate the protein. Despite considerable advances in this field, methodologies to sensitize tumors by depleting AGT and the selection of the appropriate chemotherapeutic agent to be combined with AGT depleting drugs are still under evaluation.

An additional important issue in combining DNA alkylating agents with AGT inhibitors is whether to include such inhibitors in the treatment of tumors with no or low AGT content, especially because such a combination limits the dose of the alkylating agent. Dose is important for several reasons, including the fact that the alkylating agent itself might quench low levels of AGT. A case in point is TMZ, which at a dose of 100 mg/kg eliminates all of the AGT activity in tumors having moderate AGT levels for a prolonged time period (Chinnasamy et al., Blood, 89: 1566-1573, 1997). In addition, the inverse correlation between AGT levels and effectiveness of BCNU against central nervous system tumors (Belanisch et al., Cancer Res., 56: 783-788, 1996; Jaeckle et al., J. Clin. Oncol., 16: 3310-3315, 1998) suggest that there may be no benefit in treating AGT-deficient tumors with AGT inhibitors. Determining the threshold of AGT activity that could be overcome by alkylating agents without the use of AGT inhibitors may be beneficial.

High AGT activity confers resistance to DNA alkyating agents (see above). A sensitive and fast turn-round AGT assay could be used to select patients with low AGT activities, and thus provide a better outcome for patients receiving DNA alkylating agents. A few assays have been developed but they are either not sensitive enough or so labor-intensive that they are not suitable for routine laboratory use (Wu et al., Cancer Res., 47: 6229, 1987; Gerson et al., J. clin. Invest., 76:2106, 1985; Kreklau et al., Nucleic Acid Res., 29:2558, 2001).

This invention provides an improved assay, which is simple and efficient, for alkylguanyltransferase.

SUMMARY OF THE INVENTION

This invention provides a method to determine alkylguanyltransferase (AGT) activity in a sample, comprising steps of:
  (a) placing the sample in an appropriate condition so that the AGT is functional;
  (b) contacting the sample with an alkylguanyltransferase detector (AGTD) under conditions permitting the binding of AGT and AGTD to produce a signal; and
  (c) measuring the signal, thereby determining the AGT activity in said sample.

This invention provides an AGTD which contains:
  (a) a AGT binder; and
  (b) a detectable signal; and optionally,
  (c) a system that detect the signal which subsequently generates a second signal.

The first or second signal, in the form of color, light, fluorescence, or radioactivity, is then detected with the corresponding methods.

Finally, this invention provides different uses of the above method.

DETAILED DESCRIPTION OF THE FIGURES

FIG. 1. Detection of AGT activity
FIG. 2. Signal molecule conjugated to EX
FIG. 3. Signal molecule conjugated to AP
FIG. 4. Signal molecule conjugated to O6BG
FIG. 5. Scintillation Proximity Assay

DETAILED DESCRIPTION OF THE INVENTION

This invention provides a method to determine AGT activity in a sample, comprising steps of:
  (d) placing the sample in an appropriate condition so that the AGT is functional;
  (e) contacting the sample with an AGTD under conditions permitting the binding of AGT and AGTD to produce a signal; and
  (f) measuring the signal, thereby determining the AGT activity in said sample.

In an embodiment, the sample is from a patient. As used herein, AGTD comprises:
  (d) a AGT binder;
  (e) a detectable signal; and optionally,
  (f) a system that detect the signal which subsequently generates a second signal.

AGTD may carry more than one signal. The signal may be detected directly or indirectly. For indirect detection, other agent(s) may be used to facilitate said detection. For example, the detectable signal may include an antibody which would be recognized by a second antibody. The second antibody is linked to a marker which is detected by standard methods.

The current assay employs an agent (AGT binder) that binds to AGT, which is capable of transferring a chemical moiety from the AGT binder to AGT. The AGT binder can be an agonist, antagonist, activator, or inhibitor of AGT.

These agents include but not limit to $N^1$, $O^6$-ethanoxanthosine (EX) (Noll and Clarke, Nucleic Acid Res., 29: 4025, 2001), 2'-deoxy-6-(cystamine)-2-aminopurine (AP) (Paalman et al., Nucleic Acid Res., 25:1795, 1997), temozolomide, benzylguinine, O(6)-Benzylguanine (O6BG), 8-aza-O(6)-benzylguanine, O(6)-(4-bromophenyl)-guanine (O6BTG), O(6)alkylguanine, and analogues of these agents. AGT binder also includes DNA or oligoribonucleotide or oligodeoxyribonucletide (collectively called oligonucleotide) containing the above agents.

In one embodiment, the chemical moiety transferred from AGT binder to AGT contains a signal such as radioactivity, fluorescence, luminescence, or electro-spin resonance (ESR). The signal transferred from AGT binder to AGT is directly determined by various methods according to the signal transferred. In another embodiment, the chemical moiety transferred to AGT is indirectly detected with an immunoassay or other affinity binding assay (FIG. 1).

The AGT binder includes an inhibitor or activator of AGT. In an embodiment, the AGT binder is EX and the AGTD is biotin-conjugated EX (FIG. 2). In another embodiment, the AGT binder is AP and the AGTD is biotin-conjugated AP (FIG. 3). In yet other embodiment, the AGT binder is O6BG and the AGTD is biotin-conjugated O6BG (FIG. 4).

In a separable embodiment, the detectable signal molecule is a fluorophore.

Figure 5:
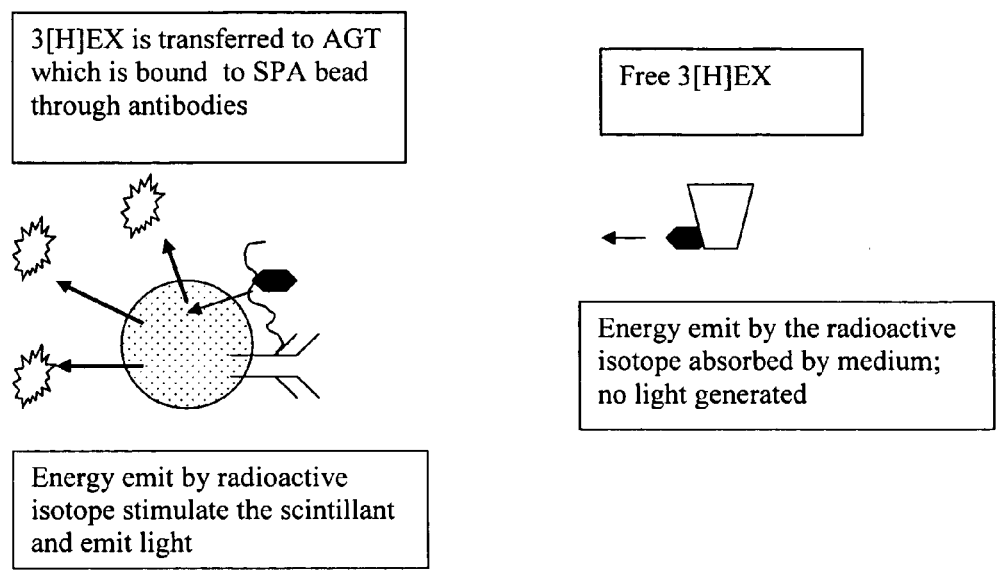

The invention also provides a method to determine AGT activity, which comprises: a) AGT, b) an AGT binder carrying a radioactive molecule which is transferred to AGT, and Scintillation Proximity Assay (SPA) bead that binds AGT directly or indirectly (FIG. 4). In a further embodiment, the AGT binder is radioactive-labeled EX or AP.

The invention provides a method to determine AGT activity, comprising of AGT and an AGT binder carrying a chemical moiety which is transferred to AGT and the chemical moiety transferred to AGT is detected by streptavidin or an antibody.

This invention provides AGTDs which are not previously known.

This invention also provides a kit with a compartment containing AGTD.

This invention will be better understood from the examples which follow. However, one skilled in the art will readily appreciate that the specific methods and results discussed are merely illustrative of the invention as described more fully in the claims which follow thereafter.

EXAMPLE 1

Scintillation Proximity Assay (SPA)

SPA beads are microscopic beads contain a scintillant that can be excite by radioactive signals to emit light. This excitation event occurs when radiolabeled molecules of interest are bound to the surface of the bead, either directly or indirectly (see FIG. 5); the light emitted can be detected with a scintillation counter.

Preparation of reagents. EX, labeled with 3[H] at various positions at the guanine moiety is used as the AGT binder.

The AGT-specific monoclonal antibody (clone MT 3.1) (NeoMarkers, Fremont, Calif.) is used to capture AGT. SPA beads coated with anti-mouse antibody is used to bind the MT3.1 anti-AGT antibody. The guanine moiety containing 3[H] is transferred from the AGT binder to anti-AGT antibody and subsequently is captured by SPA beads.

Assay. Samples containing AGT, undiluted or diluted up to 1000×, is added to a buffer containing a) 3[H]EX (1 fmol to 100 nmol), anti-AGT antibody (MT 3.1, 1 ng to 1 ug), and anti-mouse SPA bead (e.g. antimouse YSi bead, 1 ug to 10 mg, Amershan Bioscience). SPA beads coated with Protein A or Protein G can also be used. The solution is incubated for 15 to 60 minutes and radioactivity is determined with a scintillation counter. AGT activity is presented as dpm per mg protein. A précised AGT unit is determined by using 3[H]EX standard for constructing a standard curve. In this case, AGT activity is defined as fmol EX per mg protein. AGT activity can also be expressed as per DNA or cell number basis. An alternative method is to use biotin labeled anti-AGT antibody and streptavidin coated SPA beads. EX can also be labeled with other radioactive isotopes or at other positions.

EXAMPLE 2

Immunoassay

This assay is based on using two antibodies or one antibody and streptavidin; one captures AGT and the other detects the chemical moiety transferred to AGT.

Preparation of reagents. The AGT-specific monoclonal antibody (clone MT 3.1) (NeoMarkers, Fremont, Calif.) is used to coat a 96-well plate to capture AGT. Streptavidin-conjugated peroxidase is used to detect the chemical moiety transferred to AGT.

Assay. This assay is based on a sandwich Elisa assay (Chapter 14, Antibodies, A laboratory Manual, Harlow and Lane, Cold Spring Harbor Laboratory, 1988). Samples containing AGT, undiluted or diluted up to 1000×, is added to a buffer containing biotin-conjugated EX (1 fmol to 100 nmol). The solution is incubated for 15 to 60 minutes; the incubation is stopped by the addition of a buffer with or without a detergent (e.g. 0.1% SDS or 0.1% NP40). The solution is added to the plate that coated with anti-AGT antibody and further incubated for 15 to 60 minutes. The plate is washed three times with a buffer containing a mild detergent. Streptavidin-conjugated peroxidase, at various dilution is added to the well and incubated for 15 to 60 minutes. The amount of biotin-conjugated EX bound to the AGT is determined by standard Elisa methods. AGT activity is presented as O.D. per mg protein. A précised AGT unit is determined by using biotin-conjugated EX standard for constructing a standard curve. In this case, AGT activity is defined as fmol EX per mg protein. AGT activity can also be expressed as per DNA or cell number basis.

EXAMPLE 3

Fluorescence Assay

The chemical moiety transferred from AGT binder to AGT contains a fluorophore (e.g. fluorescein, Texas red; Handbook of fluorescent probes and research products (P. 62 and P15, Haugland, $9^{th}$ ed., Molecular Probes, Eugene, Oreg.).

Preparation of the AGTD. A fluorescein molecule (Molecular Probe) is used to conjugate to the 8- or 9-position of the guanine moiety of EX (FIG. 3).

Assay. Samples containing AGT, undiluted or diluted up to 1000×, is added to the AGTD, at concentrations from 1 fmol/mg protein to 10000 fmol/mg protein. Molar ratio of AGT to AGTD is ranging from 1 to 1000, preferably from 5 to 200. AGT is incubated with AGTD in a buffer that maximize AGT activity. AGT activity is determined with a fluorescence spectrophotometer. For fluorescein, the excitation and emission wavelengths are 494 nm and 518 nm, respectively. AGT activity is presented as fluorescence unit per mg protein. A précised AGT unit is determined by using EX conjugated with fluorescein as standard for constructing a standard curve. In this case, AGT activity is defined as fmol EX per mg protein. AGT activity can also be expressed as per DNA or cell number basis.

Other detecting method such as fluorescence polarization or time-resolved fluorescence spectroscopy can also be used.

What is claimed is:

1. An assay for determining the level of alkylguanyltransferase(AGT) in a sample, comprising:
   (a) contacting the sample with a biotin-conjugated AGT binder under conditions permitting formation of a biotinylated AGT binder-AGT complex;
   (b) contacting the sample in (a) with an immobilized anti-AGT antibody, under conditions permitting the anti-AGT antibody to capture the biotinylated AGT binder-AGT complex; and
   (c) contacting the captured biotinylated AGT binder-AGT complex with streptavidin conjugated to either a peroxidase or a fluorophore under conditions permitting streptavidin to bind to the captured biotinylated AGT-complex; and
   (d) removing unbound streptavidin from streptavidin bound to the captured biotinylated AGT binder-AGT complex,
   wherein the amount of peroxidase or fluorophore bound to the captured biotinylated AGT binder-AGT complex is indicative of the level of AGT in the sample.

2. The method of claim 1 wherein the streptavidin is conjugated to a fluorophore.

3. The method of claim 2 wherein the fluorophore is either fluorescein or TEXAS RED® (sulforhodamine 101).

4. The method of claim 3 wherein the streptavidin is conjugated to peroxidase.

5. The method of claim 1 wherein the immobilized anti-AGT antibody is attached to an antibody-binding SPA bead or 96-well plate.

6. The method of claim 5 wherein the anti-AGT antibody is a monoclonal antibody.

7. The method of claim 5 wherein the SPA bead comprises a scintillant.

8. The method of claim 1, wherein the ACT moiety of the biotinylated ACT binder is $N^1$, $O^6$-ethanoxanthosine (EX), $O^6$-benzylguanine (O6BG), or 2'-deoxy-6-(cystamine)-2-amino-purine (AP).

9. The method of claim 8, wherein the AGT moiety of the biotinylated AGT binder is EX.

10. The method of claim 1, wherein the anti-AGT antibody is a monoclonal antibody.

11. The method of claim 1 wherein the immobilized anti-AGT antibody is directly attached to a multiwell plate.

12. The method of claim 1 wherein the immobilized anti-AGT antibody is attached to a 96-well plate.

13. An assay for determining the level of alkylguanyltransferase (AGT) in a sample, comprising:
    (a) contacting the sample with a radioactive AGT binder under conditions permitting formation of a radioactive AGT binder-AGT complex;
    (b) contacting the sample in (a) with an anti-AGT antibody that is attached to an insoluble support, under conditions permitting the anti-AGT antibody to capture the radioactive AGT binder-AGT complex on the insoluble support; and
    (c) removing radioactive AGT binder that is not part of the radioactive AGT binder-AGT complex,
    wherein the insoluble support comprises a scintillant, and the amount of light emission stimulated by the captured radioactive AGT binder-AGT complex is indicative of the level of AGT in the sample.

14. The method of claim 13 wherein the radioactive AGT binder is radioactive EX.

15. The method of claim 14 wherein the radioactive AGT binder comprises at least one tritium ($^3$H) atom.

16. The method of claim 15 wherein the radioactive AGT binder is [$^3$H]EX.

17. An assay for determining the level of alkylguanyltransferase (AGT) in a sample, comprising:
    (a) contacting the sample with [$^3$H]EX under conditions permitting formation of a [$^3$H]EX-AGT complex;
    (b) contacting the sample in (a) with monoclonal anti-AGT antibody that is attached to a SPA bead, under conditions permitting the anti-AGT antibody to capture the [$^3$H]EX-AGT complex on the SPA bead; and
    (c) removing radioactive [$^3$H]EX that is not part of the captured [$^3$H]EX-AGT complex, wherein the SPA bead comprises a scintillant, and the amount of light emission stimulated by the captured [$^3$H]EX-AGT complex is indicative of the level of AGT in the sample.

* * * * *

UNITED STATES PATENT AND TRADEMARK OFFICE
CERTIFICATE OF CORRECTION

PATENT NO. : 7,273,714 B2 Page 1 of 1
APPLICATION NO. : 11/373623
DATED : September 25, 2007
INVENTOR(S) : Ivan C. King and Xu Lin It is certified that error appears in the above-identified patent and that said Letters Patent is hereby corrected as shown below:

In column 5, lines 44-45, "The method of claim 1, wherein the ACT moiety of the biotinylated ACT binder" should be --The method of claim 1, wherein the AGT moiety of the biotinylated AGT binder--

Signed and Sealed this

Second Day of September, 2008

JON W. DUDAS
*Director of the United States Patent and Trademark Office*